(12) United States Patent
Tonomura et al.

(10) Patent No.: US 7,569,691 B2
(45) Date of Patent: Aug. 4, 2009

(54) PROTECTED PIPERAZINO GROUP-BEARING ORGANOXYSILANE COMPOUND AND MAKING METHOD

(75) Inventors: Yoichi Tonomura, Joetsu (JP); Tohru Kubota, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 519 days.

(21) Appl. No.: 11/406,239

(22) Filed: Apr. 19, 2006

(65) Prior Publication Data

US 2006/0241294 A1    Oct. 26, 2006

(30) Foreign Application Priority Data

Apr. 20, 2005    (JP) .............................. 2005-122659

(51) Int. Cl.
*C07D 295/00*    (2006.01)
*C07D 241/04*    (2006.01)
(52) U.S. Cl. ..................................................... 544/398
(58) Field of Classification Search ............ 514/252.12; 544/398
See application file for complete search history.

(56) References Cited

U.S. PATENT DOCUMENTS

| 4,327,210 A | 4/1982 | Montavon et al. |
| 5,981,519 A | 11/1999 | Angehrn et al. |
| 2001/0037026 A1 | 11/2001 | Crameri et al. |

FOREIGN PATENT DOCUMENTS

| EP | 0355426 A2 | 8/1988 |
| EP | 0 441 530 | * 8/1991 |
| EP | 0441530 A2 | 8/1991 |
| EP | 1316557 A1 | 6/2003 |
| JP | 3414134 B2 | 4/2003 |
| WO | WO-2006/061090 A1 | 6/2006 |
| WO | WO-2006/061091 A2 | 6/2006 |

OTHER PUBLICATIONS

Journal of Organometallic Chemistry; XP-002396278; R.A. Sulzbach; Apr. 15, 1970; 24 (1970) 307-314.

* cited by examiner

*Primary Examiner*—James O Wilson
*Assistant Examiner*—Erich A Leeser
(74) *Attorney, Agent, or Firm*—Birch, Stewart, Kolasch & Birch, LLP

(57) ABSTRACT

A novel organoxysilane compound bearing a protected piperazino group is provided. It can impart rigidity, high mechanical strength, and transparency in the UV region when used in paints, adhesives and the like.

20 Claims, 4 Drawing Sheets

PROTECTED PIPERAZINO GROUP-BEARING ORGANOXYSILANE COMPOUND AND MAKING METHOD

CROSS-REFERENCE TO RELATED APPLICATION

This non-provisional application claims priority under 35 U.S.C. §119(a) on Patent Application No. 2005-122659 filed in Japan on Apr. 20, 2005, the entire contents of which are hereby incorporated by reference.

TECHNICAL FIELD

This invention relates to protected piperazino group-bearing organoxysilane compounds which are useful as paint additives, adhesives, silane coupling agents, surface treating agents or the like, and a method for preparing the same.

BACKGROUND ART

Organoxysilane compounds having protected amino groups are useful as paint additives, adhesives, silane coupling agents, surface treating agents or the like. In particular, organoxysilane compounds having silyl-protected amino groups are suited in these applications because of ease of blocking and deblocking.

Such organoxysilane compounds having silyl-protected amino groups include the N,N-bis(trimethylsilyl)aminopropyl-silane compounds described in Japanese Patent No. 3,414,134. These compounds are useful as modifiers for amino-modified silicone fluid.

The organoxysilane compounds having silyl-protected amino groups are also useful as additives to paints and adhesives. For example, they are added to epoxy resins to form one-part curable compositions having the advantages (improved adhesion and reinforcement) associated with addition of amino silane coupling agents, that is, compositions which remain stable without reactivity in moisture-barrier systems, but when contacted with moisture, undergo deblocking via hydrolysis to regenerate amino groups, exerting similar effects as observed when amino silane coupling agents are added.

When added to paints or adhesives, the organoxysilane compounds having silyl-protected amino groups are effective in that the protection of functional groups prohibits the functional groups themselves from reacting, and subsequent deblocking enables quantitative, efficient regeneration and incorporation of functional groups. However, in the recent years, rigidity, high mechanical strength, and transparency over a wide spectrum including the ultraviolet region are required for these resins, especially intended for use in optical and electronic materials. Known organoxysilane compounds having silyl-protected amino groups fail to meet satisfactory rigidity, high mechanical strength, and transparency over a wide spectrum including the ultraviolet region.

DISCLOSURE OF THE INVENTION

An object of the present invention is to provide a piperazino-bearing organoxysilane compound which can impart rigidity, high mechanical strength, and transparency over a wide spectrum including the ultraviolet region and is suited for use as paint additives, adhesives and the like.

In one aspect, the present invention provides an organoxysilane compound bearing a protected piperazino group, having the general formula (1):

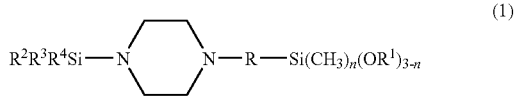

wherein R is a divalent straight or branched hydrocarbon group of 1 to 10 carbon atoms, $R^1$, $R^2$, $R^3$ and $R^4$ each are a monovalent hydrocarbon group of 1 to 10 carbon atoms, and n is 0, 1 or 2.

In another aspect, the present invention provides a method for preparing a protected piperazino group-bearing organoxysilane compound having formula (1), the method comprising the step of reacting a compound having the general formula (2) with a hydrogensilane compound having the general formula (3) in the presence of a platinum catalyst.

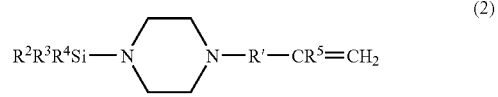

Herein $R^5$ is hydrogen or methyl, R' is a divalent straight or branched hydrocarbon group of 1 to 8 carbon atoms when $R^5$ is hydrogen, R' is a divalent straight or branched hydrocarbon group of 1 to 7 carbon atoms when $R^5$ is methyl, $R^2$, $R^3$, and $R^4$ are as defined above.

Herein $R^1$ and n are as defined above.

In a further aspect, the present invention provides a method for preparing a protected piperazino group-bearing organoxysilane compound having formula (1), the method comprising the step of silylating a compound having the general formula (4) with a silylating agent having $R^2R^3R^4Si$— group.

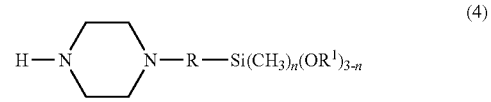

Herein R, $R^1$, $R^2$, $R^3$, $R^4$ and n are as defined above.

BENEFITS OF THE INVENTION

The use as paint additives, adhesives or the like of the protected piperazino group-bearing organoxysilane compound of the invention can impart rigidity, high mechanical strength, and transparency over a wide spectrum including the ultraviolet region.

DESCRIPTION OF THE PREFERRED EMBODIMENTS

Figure 1:
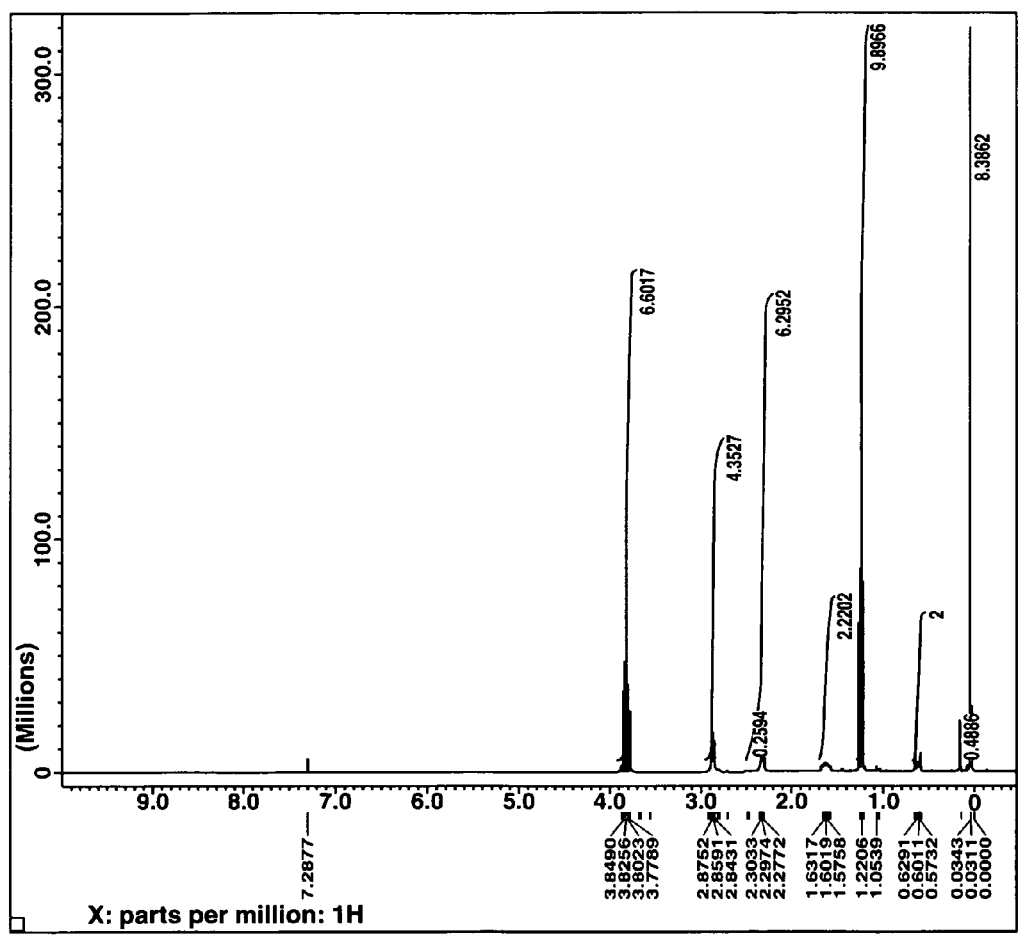
FIG. 1 is a $^1$H-NMR spectrum of the silane compound obtained in Example 1.

The compound of the invention is an organoxysilane compound bearing a protected piperazino group, having the general formula (1):

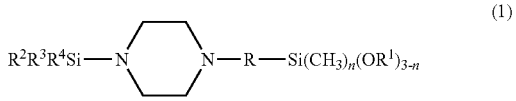

wherein R is a divalent straight or branched hydrocarbon group of 1 to 10 carbon atoms, $R^1$, $R^2$, $R^3$ and $R^4$ each are a monovalent hydrocarbon group of 1 to 10 carbon atoms, and n is 0, 1 or 2.

Specifically, $R^1$, $R^2$, $R^3$ and $R^4$ are independently selected from monovalent hydrocarbon groups of 1 to 10 carbon atoms, preferably 1 to 6 carbon atoms, including straight, branched or cyclic alkyl, alkenyl and aryl groups. Examples include methyl, ethyl, propyl, isopropyl, butyl, isobutyl, tert-butyl, pentyl, cyclopentyl, hexyl, cyclohexyl, heptyl, octyl, decyl, vinyl, allyl, methallyl, butenyl, and phenyl. R is selected from divalent straight or branched hydrocarbon groups of 1 to 10 carbon atoms, including alkylene, arylene and aralkylene groups, such as, for example, methylene, dimethylene, trimethylene, tetramethylene, hexamethylene, and isobutylene.

Illustrative, non-limiting examples of the protected piperazino group-bearing organoxysilane compound of the invention include 1-[1-(trimethoxysilyl)methyl]-4-trimethylsilylpiperazine,
1-[1-(methyldimethoxysilyl)methyl]-4-trimethylsilylpiperazine,
1-[1-(dimethylmethoxysilyl)methyl]-4-trimethylsilylpiperazine,
1-[1-(triethoxysilyl)methyl]-4-trimethylsilylpiperazine,
1-[1-(methyldiethoxysilyl)methyl]-4-trimethylsilylpiperazine,
1-[1-(dimethylethoxysilyl)methyl]-4-trimethylsilylpiperazine,
1-[1-(trimethoxysilyl)methyl]-4-triethylsilylpiperazine,
1-[1-(methyldimethoxysilyl)methyl]-4-triethylsilylpiperazine,
1-[1-(dimethylmethoxysilyl)methyl]-4-triethylsilylpiperazine,
1-[1-(triethoxysilyl)methyl]-4-triethylsilylpiperazine,
1-[1-(methyldiethoxysilyl)methyl]-4-triethylsilylpiperazine,
1-[1-(dimethylethoxysilyl)methyl]-4-triethylsilylpiperazine,
1-[1-(trimethoxysilyl)methyl]-4-t-butyldimethylsilylpiperazine,
1-[1-(methyldimethoxysilyl)methyl]-4-t-butyldimethylsilylpiperazine,
1-[1-(dimethylmethoxysilyl)methyl]-4-t-butyldimethylsilylpiperazine,
1-[1-(triethoxysilyl)methyl]-4-t-butyldimethylsilylpiperazine,
1-[1-(methyldiethoxysilyl)methyl]-4-t-butyldimethylsilylpiperazine,
1-[1-(dimethylethoxysilyl)methyl]-4-t-butyldimethylsilylpiperazine,
1-[1-(trimethoxysilyl)methyl]-4-triisopropylsilylpiperazine,
1-[1-(methyldimethoxysilyl)methyl]-4-triisopropylsilylpiperazine,
1-[1-(dimethylmethoxysilyl)methyl]-4-triisopropylsilylpiperazine,
1-[1-(triethoxysilyl)methyl]-4-triisopropylsilylpiperazine,
1-[1-(methyldiethoxysilyl)methyl]-4-triisopropylsilylpiperazine,
1-[1-(dimethylethoxysilyl)methyl]-4-triisopropylsilylpiperazine,
1-[2-(trimethoxysilyl)ethyl]-4-trimethylsilylpiperazine,
1-[2-(methyldimethoxysilyl)ethyl]-4-trimethylsilylpiperazine,
1-[2-(dimethylmethoxysilyl)ethyl]-4-trimethylsilylpiperazine,
1-[2-(triethoxysilyl)ethyl]-4-trimethylsilylpiperazine,
1-[2-(methyldiethoxysilyl)ethyl]-4-trimethylsilylpiperazine,
1-[2-(dimethylethoxysilyl)ethyl]-4-trimethylsilylpiperazine,
1-[2-(trimethoxysilyl)ethyl]-4-triethylsilylpiperazine,
1-[2-(methyldimethoxysilyl)ethyl]-4-triethylsilylpiperazine,
1-[2-(dimethylmethoxysilyl)ethyl]-4-triethylsilylpiperazine,
1-[2-(triethoxysilyl)ethyl]-4-triethylsilylpiperazine,
1-[2-(methyldiethoxysilyl)ethyl]-4-triethylsilylpiperazine,
1-[2-(dimethylethoxysilyl)ethyl]-4-triethylsilylpiperazine,
1-[2-(trimethoxysilyl)ethyl]-4-t-butyldimethylsilylpiperazine,
1-[2-(methyldimethoxysilyl)ethyl]-4-t-butyldimethylsilylpiperazine,
1-[2-(dimethylmethoxysilyl)ethyl]-4-t-butyldimethylsilylpiperazine,
1-[2-(triethoxysilyl)ethyl]-4-t-butyldimethylsilylpiperazine,
1-[2-(methyldiethoxysilyl)ethyl]-4-t-butyldimethylsilylpiperazine,
1-[2-(dimethylethoxysilyl)ethyl]-4-t-butyldimethylsilylpiperazine,
1-[2-(trimethoxysilyl)ethyl]-4-triisopropylsilylpiperazine,
1-[2-(methyldimethoxysilyl)ethyl]-4-triisopropylsilylpiperazine,
1-[2-(dimethylmethoxysilyl)ethyl]-4-triisopropylsilylpiperazine,
1-[2-(triethoxysilyl)ethyl]-4-triisopropylsilylpiperazine,
1-[2-(methyldiethoxysilyl)ethyl]-4-triisopropylsilylpiperazine,
1-[2-(dimethylethoxysilyl)ethyl]-4-triisopropylsilylpiperazine,
1-[3-(trimethoxysilyl)propyl]-4-trimethylsilylpiperazine,
1-[3-(methyldimethoxysilyl)propyl]-4-trimethylsilylpiperazine,
1-[3-(dimethylmethoxysilyl)propyl]-4-trimethylsilylpiperazine,
1-[3-(triethoxysilyl)propyl]-4-trimethylsilylpiperazine,
1-[3-(methyldiethoxysilyl)propyl]-4-trimethylsilylpiperazine,
1-[3-(dimethylethoxysilyl)propyl]-4-trimethylsilylpiperazine,
1-[3-(trimethoxysilyl)propyl]-4-triethylsilylpiperazine,
1-[3-(methyldimethoxysilyl)propyl]-4-triethylsilylpiperazine,
1-[3-(dimethylmethoxysilyl)propyl]-4-triethylsilylpiperazine,
1-[3-(triethoxysilyl)propyl]-4-triethylsilylpiperazine,
1-[3-(methyldiethoxysilyl)propyl]-4-triethylsilylpiperazine,
1-[3-(dimethylethoxysilyl)propyl]-4-triethylsilylpiperazine,
1-[3-(trimethoxysilyl)propyl]-4-t-butyldimethylsilylpiperazine,
1-[3-(methyldimethoxysilyl)propyl]-4-t-butyldimethylsilylpiperazine,
1-[3-(dimethylmethoxysilyl)propyl]-4-t-butyldimethylsilylpiperazine, 1-[3-(triethoxysilyl)propyl]-4-t-butyldimethylsilylpiperazine,
1-[3-(methyldiethoxysilyl)propyl]-4-t-butyldimethylsilylpiperazine,
1-[3-(dimethylethoxysilyl)propyl]-4-t-butyldimethylsilylpiperazine,
1-[3-(trimethoxysilyl)propyl]-4-triisopropylsilylpiperazine,
1-[3-(methyldimethoxysilyl)propyl]-4-triisopropylsilylpiperazine,
1-[3-(dimethylmethoxysilyl)propyl]-4-triisopropylsilylpiperazine,
1-[3-(triethoxysilyl)propyl]-4-triisopropylsilylpiperazine,
1-[3-(methyldiethoxysilyl)propyl]-4-triisopropylsilylpiperazine,
1-[3-(dimethylethoxysilyl)propyl]-4-triisopropylsilylpiperazine,
1-[3-(trimethoxysilyl)-2-methylpropyl]-4-trimethylsilylpiperazine,
1-[3-(methyldimethoxysilyl)-2-methylpropyl]-4-trimethylsilylpiperazine,
1-[3-(dimethylmethoxysilyl)-2-methylpropyl]-4-trimethylsilylpiperazine,
1-[3-(triethoxysilyl)-2-methylpropyl]-4-trimethylsilylpiperazine,
1-[3-(methyldiethoxysilyl)-2-methylpropyl]-4-trimethylsilylpiperazine,
1-[3-(dimethylethoxysilyl)-2-methylpropyl]-4-trimethylsilylpiperazine,
1-[3-(trimethoxysilyl)-2-methylpropyl]-4-triethylsilylpiperazine,
1-[3-(methyldimethoxysilyl)-2-methylpropyl]-4-triethylsilylpiperazine,
1-[3-(dimethylmethoxysilyl)-2-methylpropyl]-4-triethylsilylpiperazine,
1-[3-(triethoxysilyl)-2-methylpropyl]-4-triethylsilylpiperazine,
1-[3-(methyldiethoxysilyl)-2-methylpropyl]-4-triethylsilylpiperazine,
1-[3-(dimethylethoxysilyl)-2-methylpropyl]-4-triethylsilylpiperazine,
1-[3-(trimethoxysilyl)-2-methylpropyl]-4-t-butyldimethylsilylpiperazine,
1-[3-(methyldimethoxysilyl)-2-methylpropyl]-4-t-butyldimethylsilylpiperazine,
1-[3-(dimethylmethoxysilyl)-2-methylpropyl]-4-t-butyldimethylsilylpiperazine,
1-[3-(triethoxysilyl)-2-methylpropyl]-4-t-butyldimethylsilylpiperazine,
1-[3-(methyldiethoxysilyl)-2-methylpropyl]-4-t-butyldimethylsilylpiperazine,
1-[3-(dimethylethoxysilyl)-2-methylpropyl]-4-t-butyldimethylsilylpiperazine,
1-[3-(trimethoxysilyl)-2-methylpropyl]-4-triisopropylsilylpiperazine,
1-[3-(methyldimethoxysilyl)-2-methylpropyl]-4-triisopropylsilylpiperazine,
1-[3-(dimethylmethoxysilyl)-2-methylpropyl]-4-triisopropylsilylpiperazine,
1-[3-(triethoxysilyl)-2-methylpropyl]-4-triisopropylsilylpiperazine,
1-[3-(methyldiethoxysilyl)-2-methylpropyl]-4-triisopropylsilylpiperazine,
1-[3-(dimethylethoxysilyl)-2-methylpropyl]-4-triisopropylsilylpiperazine,
1-[4-(trimethoxysilyl)butyl]-4-trimethylsilylpiperazine,
1-[4-(methyldimethoxysilyl)butyl]-4-trimethylsilylpiperazine,
1-[4-(dimethylmethoxysilyl)butyl]-4-trimethylsilylpiperazine,
1-[4-(triethoxysilyl)butyl]-4-trimethylsilylpiperazine,
1-[4-(methyldiethoxysilyl)butyl]-4-trimethylsilylpiperazine,
1-[4-(dimethylethoxysilyl)butyl]-4-trimethylsilylpiperazine,
1-[4-(trimethoxysilyl)butyl]-4-triethylsilylpiperazine,
1-[4-(methyldimethoxysilyl)butyl]-4-triethylsilylpiperazine,
1-[4-(dimethylmethoxysilyl)butyl]-4-triethylsilylpiperazine,
1-[4-(triethoxysilyl)butyl]-4-triethylsilylpiperazine,
1-[4-(methyldiethoxysilyl)butyl]-4-triethylsilylpiperazine,
1-[4-(dimethylethoxysilyl)butyl]-4-triethylsilylpiperazine,
1-[4-(trimethoxysilyl)butyl]-4-t-butyldimethylsilylpiperazine,
1-[4-(methyldimethoxysilyl)butyl]-4-t-butyldimethylsilylpiperazine,
1-[4-(dimethylmethoxysilyl)butyl]-4-t-butyldimethylsilylpiperazine,
1-[4-(triethoxysilyl)butyl]-4-t-butyldimethylsilylpiperazine,
1-[4-(methyldiethoxysilyl)butyl]-4-t-butyldimethylsilylpiperazine,
1-[4-(dimethylethoxysilyl)butyl]-4-t-butyldimethylsilylpiperazine,
1-[4-(trimethoxysilyl)butyl]-4-triisopropylsilylpiperazine,
1-[4-(methyldimethoxysilyl)butyl]-4-triisopropylsilylpiperazine,
1-[4-(dimethylmethoxysilyl)butyl]-4-triisopropylsilylpiperazine,
1-[4-(triethoxysilyl)butyl]-4-triisopropylsilylpiperazine,
1-[4-(methyldiethoxysilyl)butyl]-4-triisopropylsilylpiperazine,
1-[4-(dimethylethoxysilyl)butyl]-4-triisopropylsilylpiperazine, etc.

In one embodiment of the inventive method, the protected piperazino group-bearing organoxysilane compound having the general formula (1) is prepared by reacting a compound having the general formula (2) with a hydrogensilane compound having the general formula (3) in the presence of a platinum catalyst.

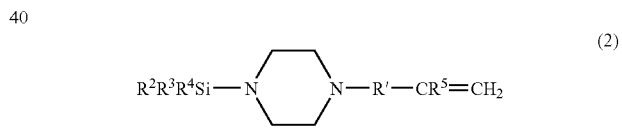

(2)

Herein $R^5$ is hydrogen or methyl, R' is a divalent straight or branched hydrocarbon group of 1 to 8 carbon atoms when $R^5$ is hydrogen, R' is a divalent straight or branched hydrocarbon group of 1 to 7 carbon atoms when $R^5$ is methyl, $R^2$, $R^3$, and $R^4$ are as defined above.

(3)

Herein $R^1$ and n are as defined above.

Specifically, R' is a divalent straight or branched hydrocarbon group of 1 to 8 carbon atoms when $R^5$ is hydrogen, and R' is a divalent straight or branched hydrocarbon group of 1 to 7 carbon atoms when $R^5$ is methyl. Examples of such hydrocarbon groups include alkylene groups such as methylene, ethylene, trimethylene, and tetramethylene, arylene groups such as phenylene, and aralkylene groups.

Illustrative, non-limiting examples of the compound having formula (2) include
1-vinyl-4-trimethylsilylpiperazine,
1-vinyl-4-triethylsilylpiperazine,
1-vinyl-4-t-butyldimethylsilylpiperazine,
1-vinyl-4-triisopropylsilylpiperazine, 1-allyl-4-trimethylsilylpiperazine,
1-allyl-4-triethylsilylpiperazine,
1-allyl-4-t-butyldimethylsilylpiperazine,
1-allyl-4-triisopropylsilylpiperazine,
1-methallyl-4-trimethylsilylpiperazine,
1-methallyl-4-triethylsilylpiperazine,
1-methallyl-4-t-butyldimethylsilylpiperazine,
1-methallyl-4-triisopropylsilylpiperazine,
1-butenyl-4-trimethylsilylpiperazine,
1-butenyl-4-triethylsilylpiperazine,
1-butenyl-4-t-butyldimethylsilylpiperazine,
1-butenyl-4-triisopropylsilylpiperazine, etc.

Illustrative, non-limiting examples of the hydrogensilane compound having formula (3) used herein include trimethoxysilane, methyldimethoxysilane, dimethylmethoxysilane, triethoxysilane, methyldiethoxysilane, and dimethylethoxysilane.

The compound having formula (2) and the hydrogensilane compound having formula (3) may be used in any blend ratio although it is preferred for better reactivity and productivity to use the hydrogensilane compound having formula (3) in an amount of 0.5 to 2 moles, more preferably 0.8 to 1.2 moles per mole of the compound having formula (2).

For the reaction, a platinum catalyst is used, examples of which include chloroplatinic acid, chloroplatinic acid in alcohol, platinum-1,3-divinyl-1,1,3,3-tetramethyldisiloxane complex in toluene or xylene, tetrakistriphenylphosphine platinum, dichlorobistriphenylphosphine platinum, dichlorobisacetonitrile platinum, dichlorobisbenzonitrile platinum, and dichlorocyclooctadiene platinum. The amount of the platinum catalyst used is not particularly limited although it is preferred for better reactivity and productivity to use 0.000001 to 0.01 mole, especially 0.00001 to 0.001 mole of the platinum catalyst per mole of the compound having formula (2).

The reaction is preferably carried out at a temperature of 0° C. to 120° C., more preferably 20° C. to 100° C., for a time of about 1 to about 20 hours, more preferably about 1 to about 10 hours although these parameters are not critical.

It is understood that the reaction can proceed without solvent although a solvent may be used. Examples of suitable solvents, if used, include hydrocarbon solvents such as pentane, hexane, cyclohexane, heptane, isooctane, benzene, toluene, and xylene; ether solvents such as diethyl ether, tetrahydrofuran and dioxane; ester solvents such as ethyl acetate and butyl acetate; aprotic polar solvents such as acetonitrile and N,N-dimethylformamide; and chlorinated hydrocarbon solvents such as dichloromethane and chloroform. These solvents may be used alone or in admixture.

In another embodiment of the inventive method, the protected piperazino group-bearing organoxysilane compound having formula (1) is prepared by silylating a compound having the general formula (4) with a silylating agent having $R^2R^3R^4Si-$ group wherein $R^2$, $R^3$ and $R^4$ are as defined above.

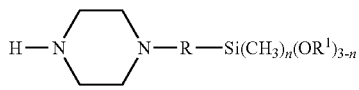

(4)

Herein R is a divalent straight or branched hydrocarbon group of 1 to 10 carbon atoms, $R^1$ is a monovalent hydrocarbon group of 1 to 10 carbon atoms, and n is 0, 1 or 2.

Illustrative, non-limiting examples of the compound having formula (4) include
1-[1-(trimethoxysilyl)methyl]piperazine,
1-[1-(methyldimethoxysilyl)methyl]piperazine,
1-[1-(dimethylmethoxysilyl)methyl]piperazine,
1-[1-(triethoxysilyl)methyl]piperazine,
1-[1-(methyldiethoxysilyl)methyl]piperazine,
1-[1-(dimethylethoxysilyl)methyl]piperazine,
1-[2-(trimethoxysilyl)ethyl]piperazine,
1-[2-(methyldimethoxysilyl)ethyl]piperazine,
1-[2-(dimethylmethoxysilyl)ethyl]piperazine,
1-[2-(triethoxysilyl)ethyl]piperazine,
1-[2-(methyldiethoxysilyl)ethyl]piperazine,
1-[2-(dimethylethoxysilyl)ethyl]piperazine,
1-[3-(trimethoxysilyl)propyl]piperazine,
1-[3-(methyldimethoxysilyl)propyl]piperazine,
1-[3-(dimethylmethoxysilyl)propyl]piperazine,
1-[3-(triethoxysilyl)propyl]piperazine,
1-[3-(methyldiethoxysilyl)propyl]piperazine,
1-[3-(dimethylethoxysilyl)propyl]piperazine,
1-[3-(trimethoxysilyl)-2-methylpropyl]piperazine,
1-[3-(methyldimethoxysilyl)-2-methylpropyl]piperazine,
1-[3-(dimethylmethoxysilyl)-2-methylpropyl]piperazine,
1-[3-(triethoxysilyl)-2-methylpropyl]piperazine,
1-[3-(methyldiethoxysilyl)-2-methylpropyl]piperazine,
1-[3-(dimethylethoxysilyl)-2-methylpropyl]piperazine,
1-[4-(trimethoxysilyl)butyl]piperazine,
1-[4-(methyldimethoxysilyl)butyl]piperazine,
1-[4-(dimethylmethoxysilyl)butyl]piperazine,
1-[4-(triethoxysilyl)butyl]piperazine,
1-[4-(methyldiethoxysilyl)butyl]piperazine,
1-[4-(dimethylethoxysilyl)butyl]piperazine, etc.

Exemplary of the silylating agent used in the above reaction are triorganohalosilanes having the formula: $R^2R^3R^4SiX$ (wherein $R^2$, $R^3$, and $R^4$ are as defined above and X is a halogen atom such as chlorine) such as trimethylchlorosilane, trimethylbromosilane, trimethyliodosilane, triethylchlorosilane, t-butyldimethylchlorosilane, and triisopropylchlorosilane, disilazanes having the formula: $(R^2R^3R^4Si)_2NH$ (wherein $R^2$, $R^3$, and $R^4$ are as defined above) such as hexamethyldisilazane and hexaethyldisilazane, and other silazanes.

The compound having formula (4) and the silylating agent may be used in any blend ratio although it is preferred for better reactivity and productivity to use the silylating agent in such an amount as to give 0.5 to 4 moles, more preferably 0.8 to 2 moles of silyl groups per mole of the compound having formula (4).

The reaction is preferably carried out at a temperature of 0° C. to 150° C., more preferably 20° C. to 130° C., for a time of about 1 to about 20 hours, more preferably about 1 to about 10 hours although these parameters are not critical.

It is understood that the reaction can proceed without solvent although a solvent may be used. Examples of suitable solvents, if used, include hydrocarbon solvents such as pentane, hexane, cyclohexane, heptane, isooctane, benzene, toluene, and xylene; ether solvents such as diethyl ether, tetrahydrofuran and dioxane; ester solvents such as ethyl acetate and butyl acetate; aprotic polar solvents such as acetonitrile and N,N-dimethylformamide; and chlorinated hydrocarbon solvents such as dichloromethane and chloroform. These solvents may be used alone or in admixture.

EXAMPLE

Examples of the invention are given below by way of illustration and not by way of limitation.

Synthesis Example 1

Synthesis of 1-allyl-4-trimethylsilylpiperazine

A flask equipped with a stirrer, reflux condenser, dropping funnel and thermometer was charged with 126.2 g (1.0 mole) of allylpiperazine, 111.3 g (1.1 moles) of triethylamine, and 300 ml of toluene. To the flask at 20-30° C., 119.5 g (1.1 moles) of trimethylchlorosilane was added dropwise over one hour. Stirring was continued for a further one hour at the temperature. With the resulting salt filtered off, the filtrate was distilled. There was obtained 168.9 g (yield 85%) of a fraction having a boiling point of 82° C./1 kPa, which was 1-allyl-4-trimethylsilylpiperazine.

Example 1

Synthesis of 1-[3-(triethoxysilyl)propyl]-4-trimethylsilylpiperazine

A flask equipped with a stirrer, reflux condenser, dropping funnel and thermometer was charged with 99.2 g (0.5 mole) of 1-allyl-4-trimethylsilylpiperazine and 0.65 g of a toluene solution of platinum-1,3-divinyl-1,1,3,3-tetramethyldisiloxane complex (platinum content 3 wt %) and heated at 70° C. Once the internal temperature became constant, 82.2 g (0.5 mole) of triethoxysilane was added dropwise over 4 hours. Stirring was continued for a further one hour at the temperature. The reaction solution was distilled, collecting 137.5 g of a fraction having a boiling point of 119-122° C./50 Pa.

Figure 2:
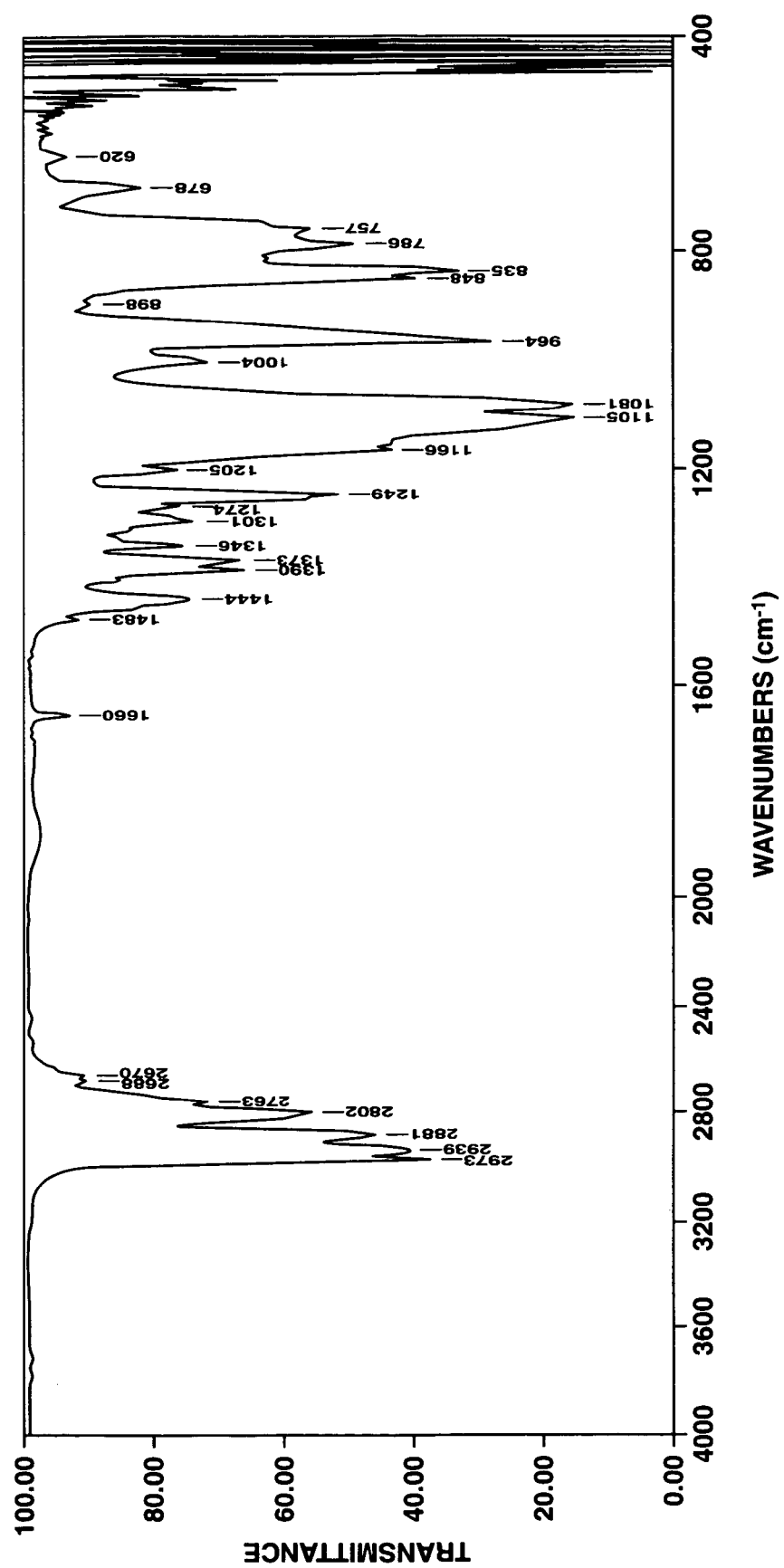
FIG. 2 is an IR spectrum of the silane compound obtained in Example 1.

The fraction was analyzed by mass spectrometry, $^1$H-NMR spectroscopy (heavy chloroform solvent) and IR spectroscopy. The data of mass spectrometry is shown below. FIG. 1 shows a $^1$H-NMR spectral chart, and FIG. 2 shows an IR spectral chart.

Mass spectrum: m/z 362, 347, 171, 128, 73

These data prove that the compound is 1-[3-(triethoxysilyl)propyl]-4-trimethylsilylpiperazine.

Example 2

Synthesis of 1-[3-(methyldiethoxysilyl)propyl]-4-trimethylsilylpiperazine

A flask equipped with a stirrer, reflux condenser, dropping funnel and thermometer was charged with 99.2 g (0.5 mole) of 1-allyl-4-trimethylsilylpiperazine and 0.65 g of a toluene solution of platinum-1,3-divinyl-1,1,3,3-tetramethyldisiloxane complex (platinum content 3 wt %) and heated at 70° C. Once the internal temperature became constant, 67.1 g (0.5 mole) of methyldiethoxysilane was added dropwise over 4 hours. Stirring was continued for a further one hour at the temperature. The reaction solution was distilled, collecting 130.8 g of a fraction having a boiling point of 105-106° C./30 Pa.

Figure 3:
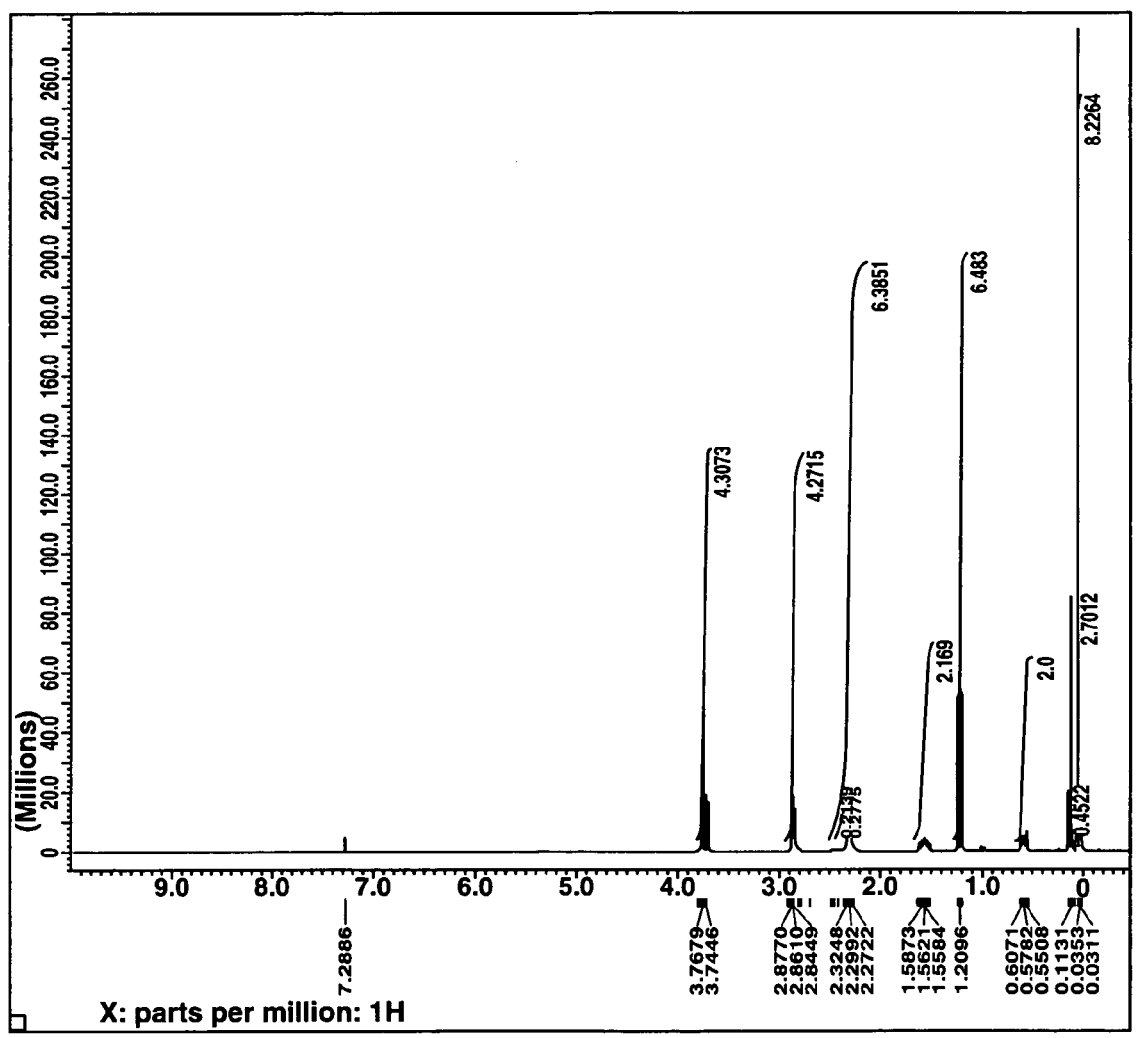
FIG. 3 is a $^1$H-NMR spectrum of the silane compound obtained in Example 2.
Figure 4:
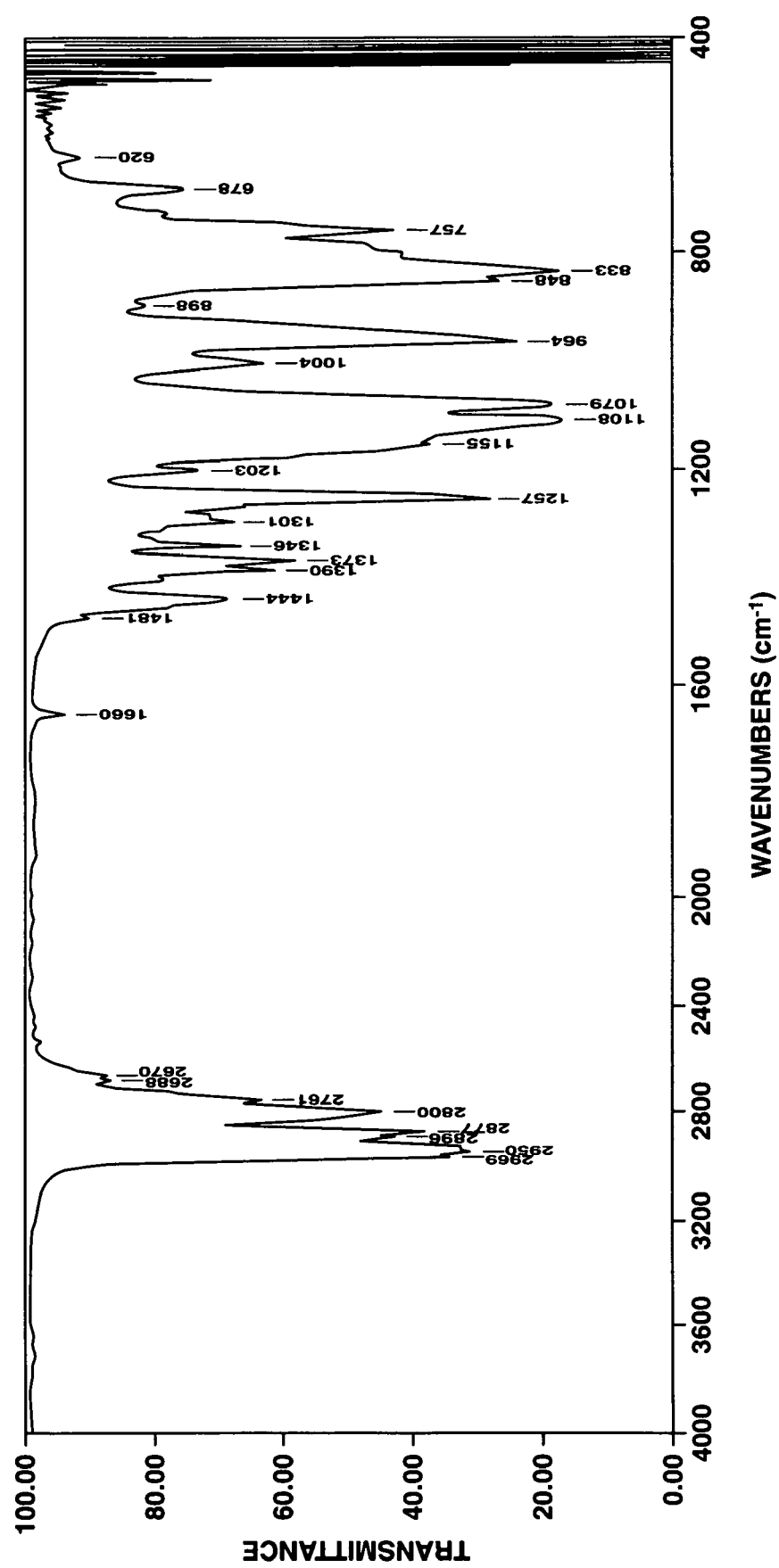
FIG. 4 is an IR spectrum of the silane compound obtained in Example 2.

The fraction was analyzed by mass spectrometry, $^1$H-NMR spectroscopy (heavy chloroform solvent) and IR spectroscopy. The data of mass spectrometry is shown below. FIG. 3 shows a $^1$H-NMR spectral chart, and FIG. 4 shows an IR spectral chart.

Mass spectrum: m/z 332, 317, 171, 128, 73

These data prove that the compound is 1-[3-(methyldiethoxysilyl)propyl]-4-trimethylsilylpiperazine.

Example 3

Synthesis of 1-[3-(triethoxysilyl)propyl]-4-trimethylsilylpiperazine from 1-[3-(triethoxysilyl)propyl]piperazine A flask equipped with a stirrer, reflux condenser, dropping funnel and thermometer was charged with 58.1 g (0.2 mole) of 1-[3-(triethoxysilyl)propyl]piperazine, 22.3 g (0.22 mole) of triethylamine, and 60 ml of toluene and heated at 40° C. Once the internal temperature became constant, 22.8 g (0.21 mole) of trimethylchlorosilane was added dropwise over one hour. Stirring was continued for a further one hour at the temperature. With the resulting salt filtered off, the filtrate was distilled, collecting 59.5 g of a fraction having a boiling point of 119-120° C./50 Pa.

The fraction was analyzed by mass spectrometry, $^1$H-NMR spectroscopy and IR spectroscopy, finding the same spectra as in Example 1. These data prove that the compound is 1-[3-(triethoxysilyl)propyl]-4-trimethylsilylpiperazine.

Japanese Patent Application No. 2005-122659 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An organoxysilane compound bearing a protected piperazino group, having the general formula (1):

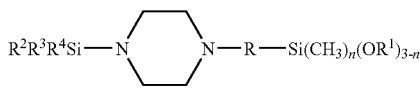

wherein R is a divalent straight or branched hydrocarbon group of 1 to 10 carbon atoms, $R^1$, $R^2$, $R^3$, and $R^4$ each are a monovalent hydrocarbon group of 1 to 10 carbon atoms, and n is 0, 1 or 2.

2. A method for preparing a protected piperazino group-bearing organoxysilane compound having the general formula (1) as set forth in claim 1, said method comprising the step of reacting a compound having the general formula (2):

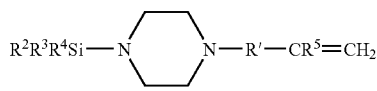

wherein $R^5$ is hydrogen or methyl, R' is a divalent straight or branched hydrocarbon group of 1 to 8 carbon atoms when $R^5$ is hydrogen, R' is a divalent straight or branched hydrocarbon group of 1 to 7 carbon atoms when $R^5$ is methyl, $R^2$, $R^3$, and $R^4$ are as defined in claim 1, with a hydrogensilane compound having the general formula (3):

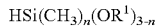

wherein $R^1$ and n are as defined in claim 1 in the presence of a platinum catalyst.

3. A method for preparing a protected piperazino group-bearing organoxysilane compound having the general formula (1) as set forth in claim 1, said method comprising the step of silylating a compound having the general formula (4):

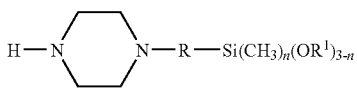

wherein R, R¹ and n are as defined in claim 1 with a silylating agent having R²R³R⁴Si— group wherein R², R³, and R⁴ are as defined in claim 1.

4. The organoxysilane compound of claim 1, wherein the R¹, R², R³, and R⁴ each are independently selected from the group of consisting of $C_{1-6}$ straight, branched or cyclic alkyl, alkenyl and aryl groups.

5. The organoxysilane compound of claim 1, wherein the R¹, R², R³, and R⁴ each includes methyl, ethyl, propyl, isopropyl, butyl, isobutyl, tert-butyl, pentyl, cyclopentyl, hexyl, cyclohexyl, heptyl, octyl, decyl, vinyl, allyl, methallyl, butenyl, and phenyl.

6. The organoxysilane compound of claim 1, wherein the R is selected from the group of consisting of $C_{1-10}$ alkylene, arylene and aralkylene groups.

7. The organoxysilane compound of claim 6, wherein the $C_{1-10}$ alkylene is selected from the group of consisting of methylene, dimethylene, trimethylene, tetramethylene, hexamethylene, and isobutylene.

8. The organoxysilane compound of claim 1, wherein the organoxysilane compound bearing the protected piperazino group, having the general formula (1) is selected from the group of consisting of:

1-[1-(trimethoxysilyl)methyl]-4-trimethylsilylpiperazine,
1-[1-(methyldimethoxysilyl)methyl]-4-trimethylsilylpiperazine,
1-[1-(dimethylmethoxysilyl)methyl]-4-trimethylsilylpiperazine,
1-[1-(triethoxysilyl)methyl]-4-trimethylsilylpiperazine,
1-[1-(methyldiethoxysilyl)methyl]-4-trimethylsilylpiperazine,
1-[1-(dimethylethoxysilyl)methyl]-4-trimethylsilylpiperazine,
1-[1-(trimethoxysilyl)methyl]-4-triethylsilylpiperazine,
1-[1-(methyldimethoxysilyl)methyl]-4-triethylsilylpiperazine,
1-[1-(dimethylmethoxysilyl)methyl]-4-triethylsilylpiperazine,
1-[1-(triethoxysilyl)methyl]-4-triethylsilylpiperazine,
1-[1-(methyldiethoxysilyl)methyl]-4-triethylsilylpiperazine,
1-[1-(dimethylethoxysilyl)methyl]-4-triethylsilylpiperazine,
1-[1-(trimethoxysilyl)methyl]-4-t-butyldimethylsilylpiperazine,
1-[1-(methyldimethoxysilyl)methyl]-4-t-butyldimethylsilylpiperazine,
1-[1-(dimethylmethoxysilyl)methyl]-4-t-butyidimethylsilylpiperazine,
1-[1-(triethoxysilyl)methyl]-4-t-butyldimethylsilylpiperazine,
1-[1-(methyldiethoxysilyl)methyl]-4-t-butyidimethylsilylpiperazine,
1-[1-(dimethylethoxysilyl)methyl]-4-t-butyidimethylsilylpiperazine,
1-[1-(trimethoxysilyl)methyl]-4-triisopropylsilylpiperazine,
1-[1-(methyldimethoxysilyl)methyl]-4-triisopropylsilylpiperazine,
1-[1-(dimethylmethoxysilyl)methyl]-4-triisopropylsilylpiperazine,
1-[1-(triethoxysilyl)methyl]-4-triisopropylsilylpiperazine,
1-[1-(methyldiethoxysilyl)methyl]-4-triisopropylsilylpiperazine,
1-[1-(dimethylethoxysilyl)methyl]-4-triisopropylsilylpiperazine,
1-[2-(trimethoxysilyl)ethyl]-4-trimethylsilylpiperazine,
1-[2-(methyldimethoxysilyl)ethyl]-4-trimethylsilylpiperazine,
1-[2-(dimethylmethoxysilyl)ethyl]-4-trimethylsilylpiperazine,
1-[2-(triethoxysilyl)ethyl]-4-trimethylsilylpiperazine,
1-[2-(methyldiethoxysilyl)ethyl]-4-trimethylsilylpiperazine,
1-[2-(dimethylethoxysilyl)ethyl]-4-trimethylsilylpiperazine,
1-[2-(trimethoxysilyl)ethyl]-4-triethylsilylpiperazine,
1-[2-(methyldimethoxysilyl)ethyl]-4-triethylsilylpiperazine,
1-[2-(dimethylmethoxysilyl)ethyl]-4-triethylsilylpiperazine,
1-[2-(triethoxysilyl)ethyl]-4-triethylsilylpiperazine,
1-[2-(methyldiethoxysilyl)ethyl]-4-triethylsilylpiperazine,
1-[2-(dimethylethoxysilyl)ethyl]-4-triethylsilylpiperazine,
1-[2-(trimethoxysilyl)ethyl]-4-t-butyldimethylsilylpiperazine,
1-[2-(methyldimethoxysilyl)ethyl]-4-t-butyldimethylsilylpiperazine,
1-[2-(dimethylmethoxysilyl)ethyl]-4-t-butyldimethylsilylpiperazine,
1-[2-(triethoxysilyl)ethyl]-4-t-butyldimethylsilylpiperazine,
1-[2-(methyldiethoxysilyl)ethyl]-4-t-butyldimethylsilylpiperazine,
1-[2-(dimethylethoxysilyl)ethyl]-4-t-butyldimethylsilylpiperazine,
1-[2-(trimethoxysilyl)ethyl]-4-triisopropylsilylpiperazine,
1-[2-(methyldimethoxysilyl)ethyl]-4-triisopropylsilylpiperazine,
1-[2-(dimethylmethoxysilyl)ethyl]-4-triisopropylsilylpiperazine,
1-[2-(triethoxysilyl)ethyl]-4-triisopropylsilylpiperazine,
1-[2-(methyldiethoxysilyl)ethyl]-4-triisopropylsilylpiperazine,
1-[2-(dimethylethoxysilyl)ethyl]-4-triisopropylsilylpiperazine,
1-[3-(trimethoxysilyl)propyl]-4-trimethylsilylpiperazine,
1-[3-(methyldimethoxysilyl)propyl]-4-trimethylsilylpiperazine,
1-[3-(dimethylmethoxysilyl)propyl]-4-trimethylsilylpiperazine,
1-[3-(triethoxysilyl)propyl]-4-trimethylsilylpiperazine,
1-[3-(methyldiethoxysilyl)propyl]-4-trimethylsilylpiperazine,
1-[3-(dimethylethoxysilyl)propyl]-4-trimethylsilylpiperazine,
1-[3-(trimethoxysilyl)propyl]-4-triethylsilylpiperazine,
1-[3-(methyldimethoxysilyl)propyl]-4-triethylsilylpiperazine,
1-[3-(dimethylmethoxysilyl)propyl]-4-triethylsilylpiperazine,
1-[3-(triethoxysilyl)propyl]-4-triethylsilylpiperazine,
1-[3-(methyldiethoxysilyl)propyl]-4-triethylsilylpiperazine,
1-[3-(dimethylethoxysilyl)propyl]-4-triethylsilylpiperazine,
1-[3-(trimethoxysilyl)propyl]-4-t-butyldimethylsilylpiperazine,
1-[3-(methyldimethoxysilyl)propyl]-4-t-butyldimethylsilylpiperazine, 1-[3-(dimethylmethoxysilyl)propyl]-4-t-butyldimethylsilylpiperazine,
1-[3-(triethoxysilyl)propyl]-4-t-butyldimethylsilylpiperazine,
1-[3-(methyldiethoxysilyl)propyl]-4-t-butyldimethylsilylpiperazine,
1-[3-(dimethylethoxysilyl)propyl]-4-t-butyldimethylsilylpiperazine,
1-[3-(trimethoxysilyl)propyl]-4-triisopropylsilylpiperazine,
1-[3-(methyldimethoxysilyl)propyl]-4-triisopropylsilylpiperazine,
1-[3-(dimethylmethoxysilyl)propyl]-4-triisopropylsilylpiperazine,
1-[3-(triethoxysilyl)propyl]-4-triisopropylsilylpiperazine,
1-[3-(methyldiethoxysilyl)propyl]-4-triisopropylsilylpiperazine,
1-[3-(dimethylethoxysilyl)propyl]-4-triisopropylsilylpiperazine,
1-[3-(trimethoxysilyl)-2-methylpropyl]-4-trimethylsilylpiperazine,
1-[3-(methyldimethoxysilyl)-2-methylpropyl]-4-trimethylsilylpiperazine,
1-[3-(dimethylmethoxysilyl)-2-methylpropyl]-4-trimethylsilylpiperazine,
1-[3-(triethoxysilyl)-2-methylpropyl]-4-trimethylsilylpiperazine,
1-[3-(methyldiethoxysilyl)-2-methylpropyl]-4-trimethylsilylpiperazine,
1-[3-(dimethylethoxysilyl)-2-methylpropyl]-4-trimethylsilylpiperazine,
1-[3-(trimethoxysilyl)-2-methylpropyl]-4-triethylsilylpiperazine,
1-[3-(methyldimethoxysilyl)-2-methylpropyl]-4-triethylsilylpiperazine,
1-[3-(dimethylmethoxysilyl)-2-methylpropyl]-4-triethylsilylpiperazine,
1-[3-(triethoxysilyl)-2-methylpropyl]-4-triethylsilylpiperazine,
1-[3-(methyldiethoxysilyl)-2-methylpropyl]-4-triethylsilylpiperazine,
1-[3-(dimethylethoxysilyl)-2-methylpropyl]-4-triethylsilylpiperazine,
1-[3-(trimethoxysilyl)-2-methylpropyl]-4-t-butyldimethylsilylpiperazine,
1-[3-(methyldimethoxysilyl)-2-methylpropyl]-4-t-butyldimethylsilylpiperazine,
1-[3-(dimethylmethoxysilyl)-2-methylpropyl]-4-t-butyldimethylsilylpiperazine,
1-[3-(triethoxysilyl)-2-methylpropyl]-4-t-butyldimethylsilylpiperazine,
1-[3-(methyldiethoxysilyl)-2-methylpropyl]-4-t-butyldimethylsilylpiperazine,
1-[3-(dimethylethoxysilyl)-2-methylpropyl]-4-t-butyldimethylsilylpiperazine,
1-[3-(trimethoxysilyl)-2-methylpropyl]-4-triisopropylsilylpiperazine,
1-[3-(methyldimethoxysilyl)-2-methylpropyl]-4-triisopropylsilylpiperazine,
1-[3-(dimethylmethoxysilyl)-2-methylpropyl]-4-triisopropylsilylpiperazine,
1-[3-(triethoxysilyl)-2-methylpropyl]-4-triisopropylsilylpiperazine,
1-[3-(methyldiethoxysilyl)-2-methylpropyl]-4-triisopropylsilylpiperazine,
1-[3-(dimethylethoxysilyl)-2-methylpropyl]-4-triisopropylsilylpiperazine,
1-[4-(trimethoxysilyl)butyl]-4-trimethylsilylpiperazine,
1-[4-(methyldimethoxysilyl)butyl]-4-trimethylsilylpiperazine,
1-[4-(dimethylmethoxysilyl)butyl]-4-trimethylsilylpiperazine,
1-[4-(triethoxysilyl)butyl]-4-trimethylsilylpiperazine,
1-[4-(methyldiethoxysilyl)butyl]-4-trimethylsilylpiperazine,
1-[4-(dimethylethoxysilyl)butyl]-4-trimethylsilylpiperazine,
1-[4-(trimethoxysilyl)butyl]-4-triethylsilylpiperazine,
1-[4-(methyldimethoxysilyl)butyl]-4-triethylsilylpiperazine,
1-[4-(dimethylmethoxysilyl)butyl]-4-triethylsilylpiperazine,
1-[4-(triethoxysilyl)butyl]-4-triethylsilylpiperazine,
1-[4-(methyldiethoxysilyl)butyl]-4-triethylsilylpiperazine,
1-[4-(dimethylethoxysilyl)butyl]-4-triethylsilylpiperazine,
1-[4-(trimethoxysilyl)butyl]-4-t-butyldimethylsilylpiperazine,
1-[4-(methyldimethoxysilyl)butyl]-4-t-butyldimethylsilylpiperazine,
1-[4-(dimethylmethoxysilyl)butyl]-4-t-butyldimethylsilylpiperazine,
1-[4-(triethoxysilyl)butyl]-4-t-butyldimethylsilylpiperazine,
1-[4-(methyldiethoxysilyl)butyl]-4-t-butyldimethylsilylpiperazine,
1-[4-(dimethylethoxysilyl)butyl]-4-t-butyldimethylsilylpiperazine,
1-[4-(trimethoxysilyl)butyl]-4-triisopropylsilylpiperazine,
1-[4-(methyldimethoxysilyl)butyl]-4-triisopropylsilylpiperazine,
1-[4-(dimethylmethoxysilyl)butyl]-4-triisopropylsilylpiperazine,
1-[4-(triethoxysilyl)butyl]-4-triisopropylsilylpiperazine,
1-[4-(methyldiethoxysilyl)butyl]-4-triisopropylsilylpiperazine, and
1-[4-(dimethylethoxysilyl)butyl]-4-triisopropylsilylpiperazine.

9. The method of claim 2, wherein the compound having the general formula (2) is selected from the group of consisting of:
1-vinyl-4-trimethylsilylpiperazine,
1-vinyl-4-triethylsilylpiperazine,
1-vinyl-4-t-butyldimethylsilylpiperazine,
1-vinyl-4-triisopropylsilylpiperazine,
1-allyl-4-trimethylsilylpiperazine,
1-allyl-4-triethylsilylpiperazine,
1-allyl-4-t-butyldimethylsilylpiperazine,
1-allyl-4-triisopropylsilylpiperazine,
1-methallyl-4-trimethylsilylpiperazine,
1-methallyl-4-triethylsilylpiperazine,
1-methallyl-4-t-butyldimethylsilylpiperazine,
1-methallyl-4-triisopropylsilylpiperazine,
1-butenyl-4-trimethylsilylpiperazine,
1-butenyl-4-triethylsilylpiperazine,
1-butenyl-4-t-butyldimethylsilylpiperazine, and
1-butenyl-4-triisopropylsilylpiperazine.

10. The method of claim 2, wherein the hydrogensilane compound having the general formula (3) is selected from the group of consisting of trimethoxysilane, methyldimethoxysilane, dimethylmethoxysilane, triethoxysilane, methyldiethoxysilane, and dimethylethoxysilane.

11. The method of claim 2, wherein the hydrogensilane compound having the general formula (3) is used in an amount of 0.5 to 2 moles per mole of the compound having the general formula (2).

12. The method of claim 2, wherein the platinum catalyst is selected from the group consisting of chloroplatinic acid, chloroplatinic acid in alcohol, platinum-1,3-divinyl-1,1,3,3-tetramethyldisiloxane complex in toluene or xylene, tetrakistriphenylphosphine platinum, dichlorobistriphenylphosphine platinum, dichlorobisacetonitrile platinum, dichlorobisbenzonitrile platinum, and dichlorocyclooctadiene platinum.

13. The method of claim 2, wherein the platinum catalyst is used in an amount of 0.000001 to 0.01 moles per mole of the compound having the general formula (2).

14. The method of claim 3, wherein the compound having the general formula (4) is selected from the group of consisting of:

1-[1-(trimethoxysilyl)methyl]piperazine,
1-[1-(methyldimethoxysilyl)methyl]piperazine,
1-[1-(dimethylmethoxysilyl)methyl]piperazine,
1-[1-(triethoxysilyl)methyl]piperazine,
1-[1-(methyldiethoxysilyl)methyl]piperazine,
1-[1-(dimethylethoxysilyl)methyl]piperazine,
1-[2-(trimethoxysilyl)ethyl]piperazine,
1-[2-(methyldimethoxysilyl)ethyl]piperazine,
1-[2-(dimethylmethoxysilyl)ethyl]piperazine,
1-[2-(triethoxysilyl)ethyl]piperazine,
1-[2-(methyldiethoxysilyl)ethyl]piperazine,
1-[2-(dimethylethoxysilyl)ethyl]piperazine,
1-[3-(trimethoxysilyl)propyl]piperazine,
1-[3-(methyldimethoxysilyl)propyl]piperazine,
1-[3-(dimethylmethoxysilyl)propyl]piperazine,
1-[3-(triethoxysilyl)propyl]piperazine,
1-[3-(methyldiethoxysilyl)propyl]piperazine,
1-[3-(dimethylethoxysilyl)propyl]piperazine,
1-[3-(trimethoxysilyl)-2-methylpropyl]piperazine,
1-[3-(methyldimethoxysilyl)-2-methylpropyl]piperazine,
1-[3-(dimethylmethoxysilyl)-2-methylpropyl]piperazine,
1-[3-(triethoxysilyl)-2-methylpropyl]piperazine,
1-[3-(methyldiethoxysilyl)-2-methylpropyl]piperazine,
1-[3-(dimethylethoxysilyl)-2-methylpropyl]piperazine,
1-[4-(trimethoxysilyl)butyl]piperazine,
1-[4-(methyldimethoxysilyl)butyl]piperazine,
1-[4-(dimethylmethoxysilyl)butyl]piperazine,
1-[4-(triethoxysilyl)butyl]piperazine,
1-[4-(methyldiethoxysilyl)butyl]piperazine, and
1-[4-(dimethylethoxysilyl)butyl]piperazine.

15. The method of claim 3, wherein the silylating agent includes triorganohalosilanes having the formula of $R^2R^3R^4SiX$ (wherein $R^2$, $R^3$, and $R^4$ are as defined in claim 3, and X is a halogen atom), disilazanes having the formula of $(R^2R^3R^4Si)_2NH$ (wherein $R^2$, $R^3$, and $R^4$ are as defined in claim 1) and other silazanes.

16. The method of claim 15, wherein the triorganohalosilanes are selected from the group of consisting of trimethylchlorosilane, trimethylbromosilane, trimethyliodosilane, triethylchlorosilane, t-butyldimethylchlorosilane, and triisopropylchlorosilane, and the disilazanes are selected from the group of consisting of hexamethyldisilazane and hexaethyldisilazane.

17. The method of claim 3, wherein the silylating agent is used in an amount of 0.5 to 4 moles of silyl groups per mole of the compound having the general formula (4).

18. The organoxysilane compound of claim 2, which is 1-[3-(triethoxysilyl)propyl]-4-trimethylsilylpiperazine.

19. The organoxysilane compound of claim 1, which is 1-[3-(methyldiethoxysilyl)propyl]-4-trimethylsilylpiperazine.

20. The organoxysilane compound of claim 1, which is 1-[3-(triethoxysilyl)propyl]-4-trimethylsilylpiperazine.

* * * * *